(12) United States Patent
Foerster et al.

(10) Patent No.: US 6,855,157 B2
(45) Date of Patent: Feb. 15, 2005

(54) METHOD AND APPARATUS FOR ATTACHING CONNECTIVE TISSUES TO BONE USING A KNOTLESS SUTURE ANCHORING DEVICE

(75) Inventors: Seth A. Foerster, San Clemente, CA (US); Norman S. Gordon, Irvine, CA (US)

(73) Assignee: ArthroCare Corporation, Sunnyvale, CA (US)

( * ) Notice: Subject to any disclaimer, the term of this patent is extended or adjusted under 35 U.S.C. 154(b) by 332 days.

(21) Appl. No.: 10/067,164

(22) Filed: Feb. 4, 2002

(65) Prior Publication Data

US 2003/0149448 A1 Aug. 7, 2003

(51) Int. Cl.⁷ .............................................. A61B 17/04
(52) U.S. Cl. ............................ 606/232; 606/72; 606/74
(58) Field of Search ................................ 606/232, 103, 606/151, 157, 158, 72, 74; 24/136 R, 115 A, 115 M, 132 WH, 133 R, 136 L, 136 A, 115 G, 484, 485, 488; 292/257, 323, 325, 256.6, 256.61, 256.63, 256.65

(56) References Cited

U.S. PATENT DOCUMENTS

| | | |
|---|---|---|
| 918,570 A | 4/1909 | Mather |
| 3,994,521 A | 11/1976 | Van Gompel |
| 5,037,422 A | 8/1991 | Hayhurst et al. |
| 5,224,946 A | 7/1993 | Hayhurst et al. |
| 5,324,308 A | 6/1994 | Pierce |
| 5,354,298 A | 10/1994 | Lee et al. |
| 5,383,905 A | 1/1995 | Gold et al. |
| 5,405,359 A | 4/1995 | Pierce |
| 5,480,403 A | 1/1996 | Lee et al. |
| 5,486,197 A | 1/1996 | Le et al. |
| 5,545,180 A | 8/1996 | Le et al. |
| 5,584,835 A | 12/1996 | Greenfield |
| 5,601,558 A | 2/1997 | Torrie et al. |
| 5,681,351 A | 10/1997 | Jamiolkowski et al. |
| 5,702,397 A | 12/1997 | Goble et al. |
| 5,702,398 A | 12/1997 | Tarabishy |
| 5,720,765 A | 2/1998 | Thal |
| 5,728,136 A | 3/1998 | Thal |
| 5,782,863 A | 7/1998 | Bartlett |
| 5,782,864 A | 7/1998 | Lizardi |
| 5,911,721 A | 6/1999 | Nicholson et al. |
| 5,935,129 A | 8/1999 | McDevitt et al. |
| 5,948,000 A | 9/1999 | Larsen et al. |
| 5,948,001 A | 9/1999 | Larsen |

(List continued on next page.)

OTHER PUBLICATIONS

US 6,238,418, 5/2001, Schwartz et al. (withdrawn)

*Primary Examiner*—Julian W. Woo
(74) *Attorney, Agent, or Firm*—John T. Raffle; Richard R. Batt

(57) ABSTRACT

An innovative bone anchor and methods for securing soft tissue, such as tendons, to bone, which permit a suture attachment that lies entirely beneath the cortical bone surface. Advantageously, the suturing material between the soft tissue and the bone anchor is secured without the need for tying a knot. The suture attachment to the bone anchor involves the looping of a length of suture around a pulley within the bone anchor, tightening the suture and attached soft tissue, and clamping the suture within the bone anchor. The bone anchor may be a tubular body having a lumen containing a plurality of suture-locking elements that clamp the suture therein. The locking elements may be thin and C-shaped. One or more locking plugs attached to separable actuation rods displace axially within the lumen and act on the locking elements to displace them radially. A generally uniform passage through the locking elements in their first positions converts to a smaller irregular passage after the locking plug displaces the elements to their second positions, thus effectively clamping the suture. The bone anchor further may include locking structure for securing itself within a bone cavity.

37 Claims, 9 Drawing Sheets

U.S. PATENT DOCUMENTS

| | | | |
|---|---|---|---|
| 5,957,968 A | * 9/1999 | Belden et al. | .............. 607/126 |
| 5,961,538 A | 10/1999 | Pedlick et al. | |
| 5,968,044 A | 10/1999 | Nicholson et al. | |
| 5,993,459 A | 11/1999 | Larsen et al. | |
| 6,007,566 A | 12/1999 | Wenstrom, Jr. | |
| 6,024,758 A | 2/2000 | Thal | |
| 6,056,773 A | 5/2000 | Bonutti | |
| 6,159,235 A | 12/2000 | Kim | |
| 6,206,895 B1 | 3/2001 | Levison | |
| 6,315,781 B1 | 11/2001 | Reinhardt et al. | |
| 6,319,252 B1 | 11/2001 | McDevitt et al. | |
| 2001/0008971 A1 | 7/2001 | Schwartz et al. | |

* cited by examiner

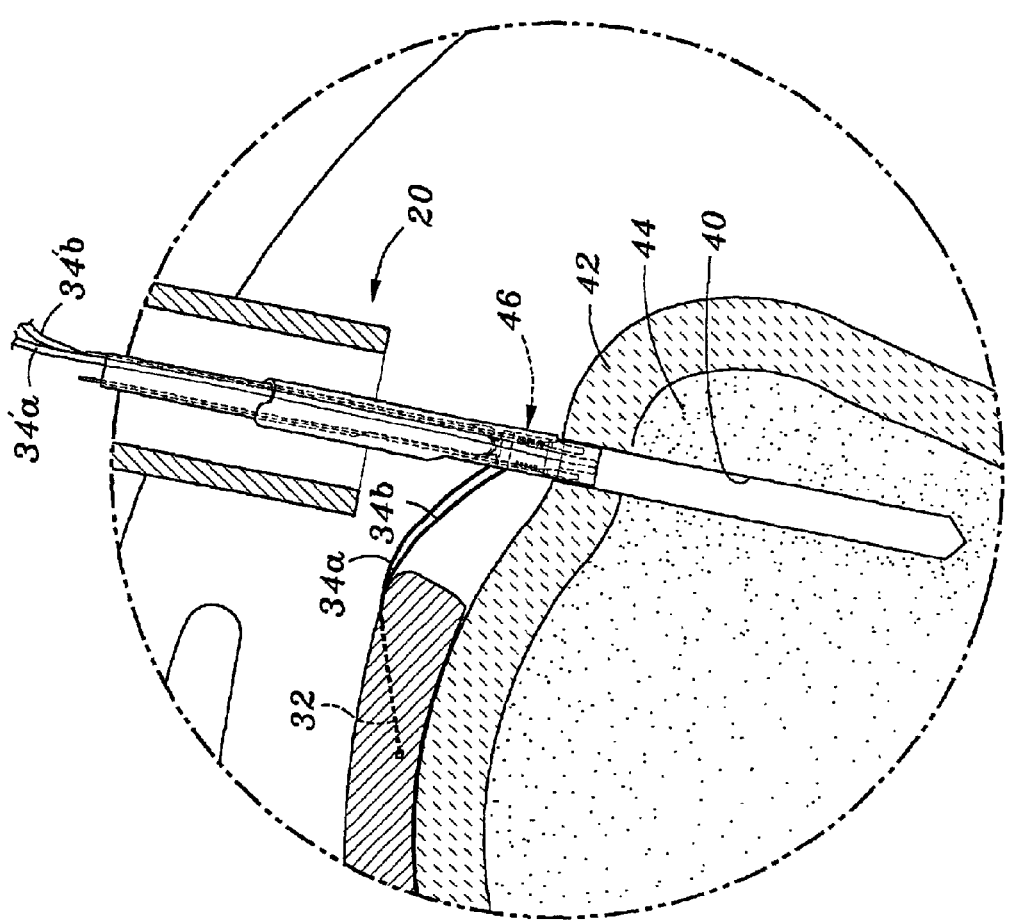
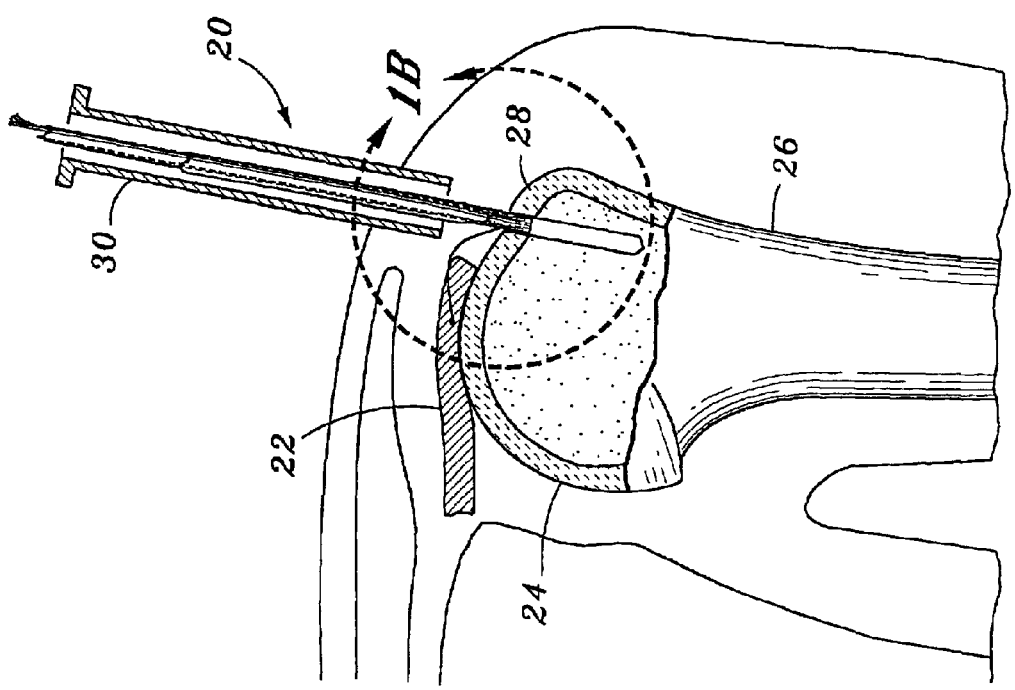

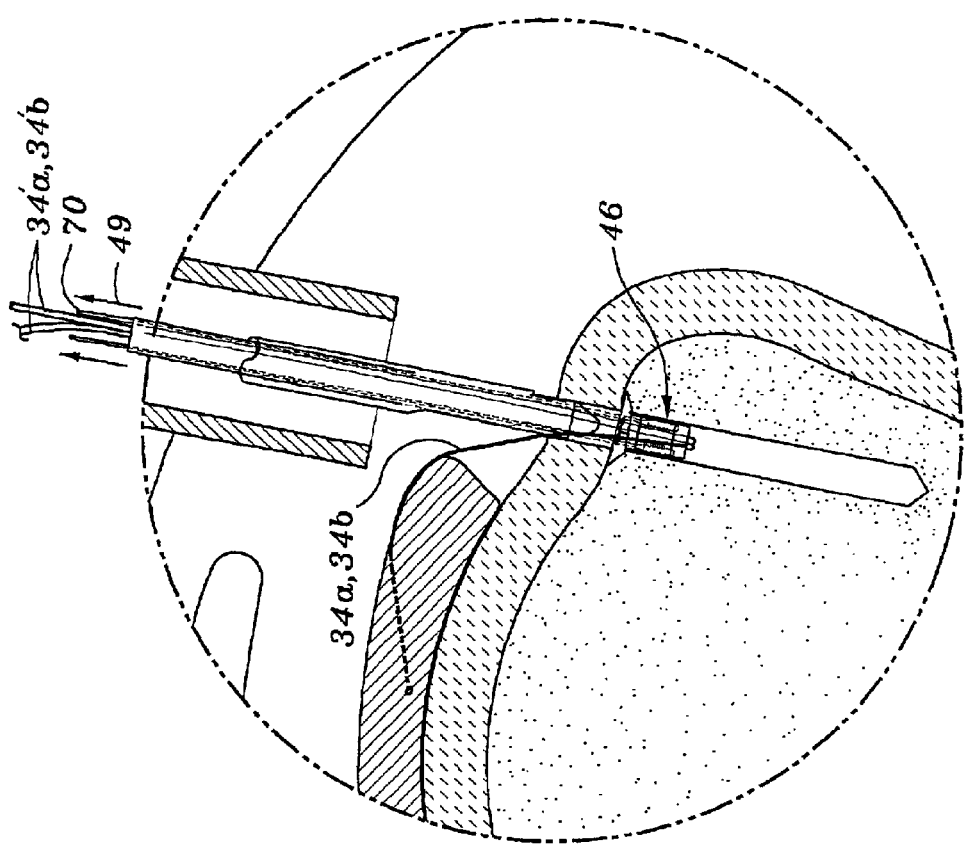
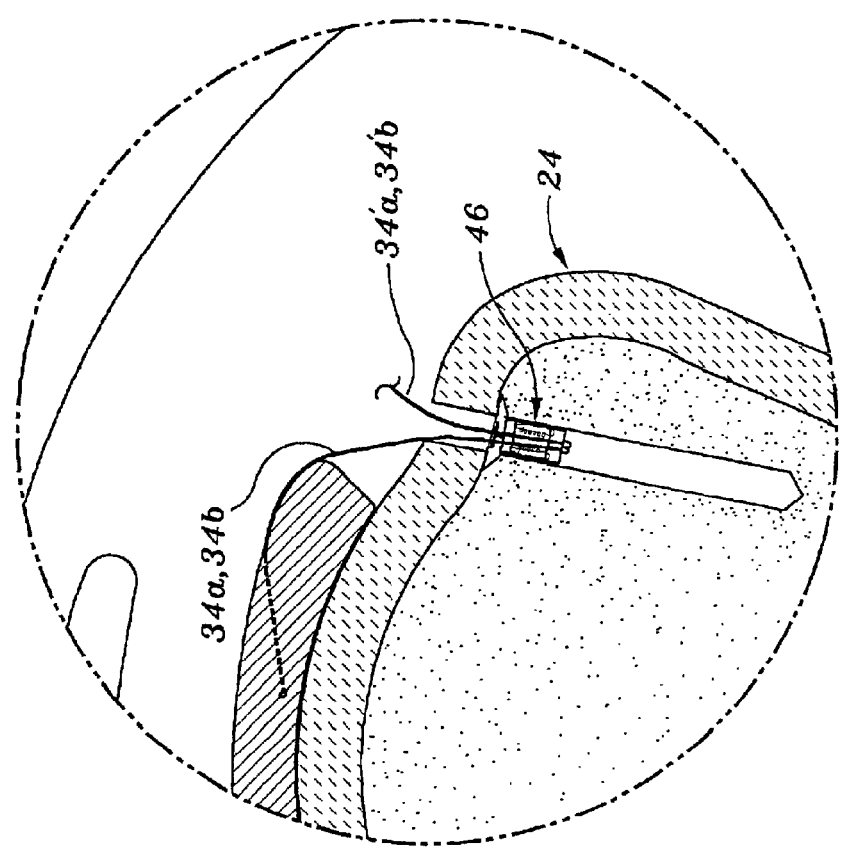
Fig. 1E
Fig. 1F

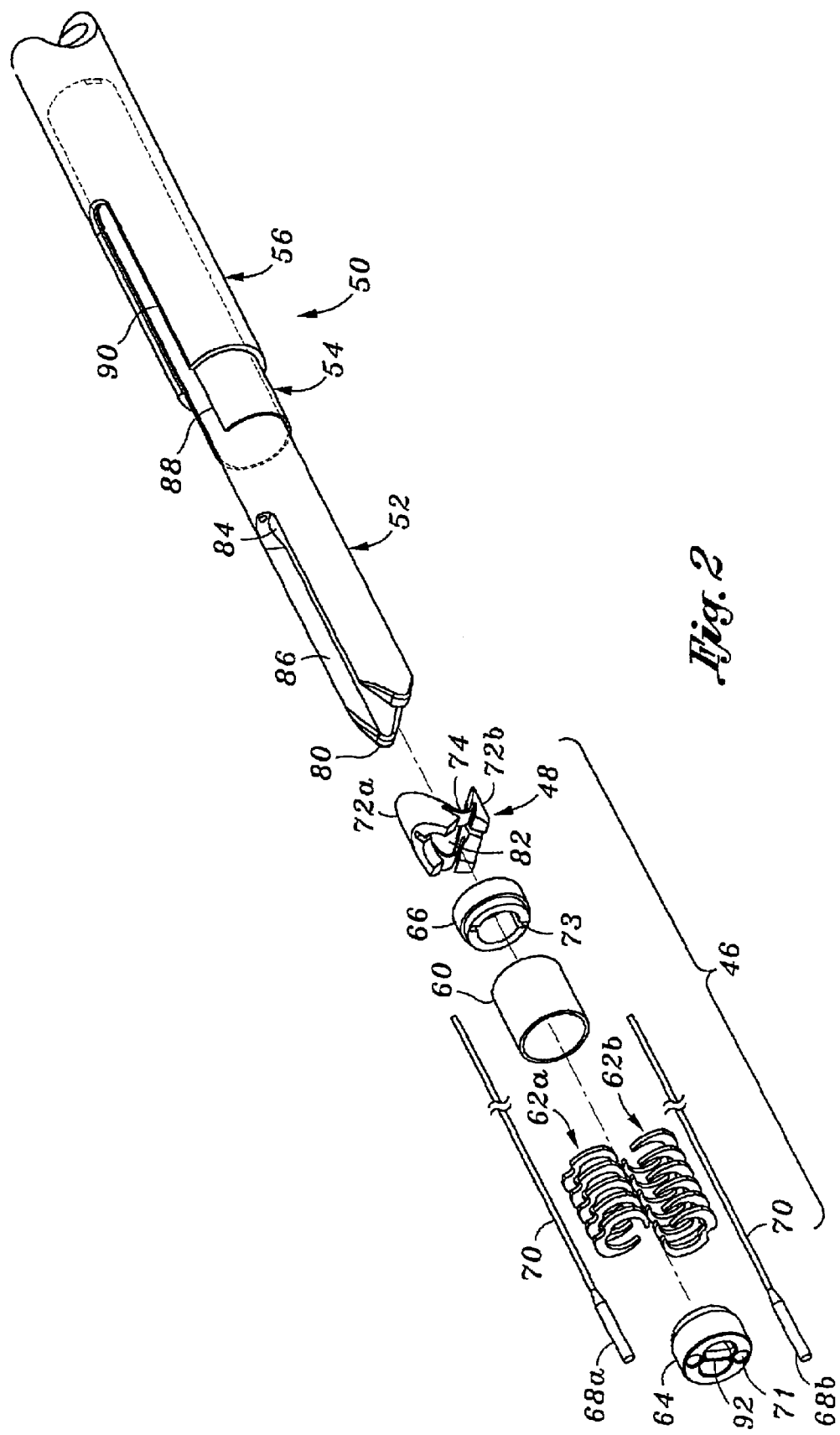

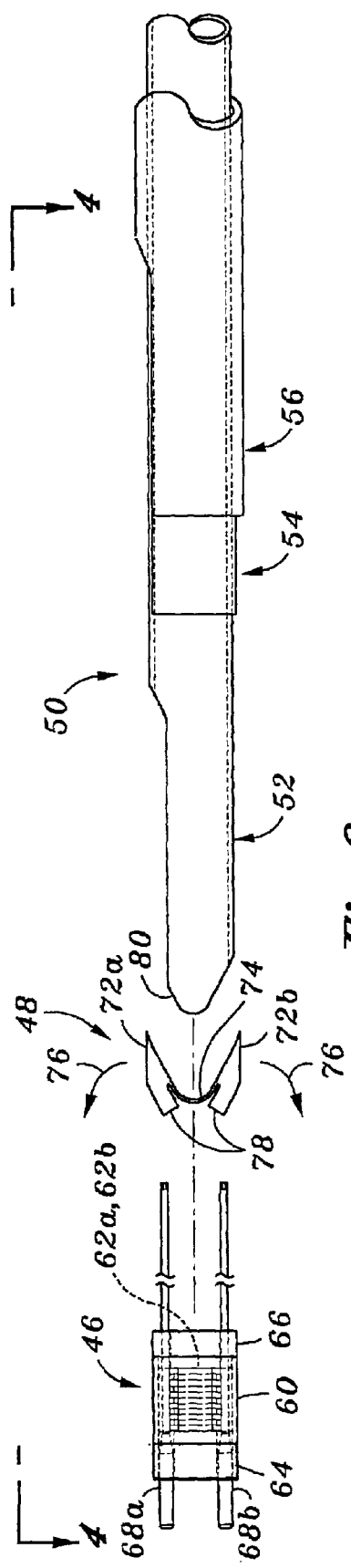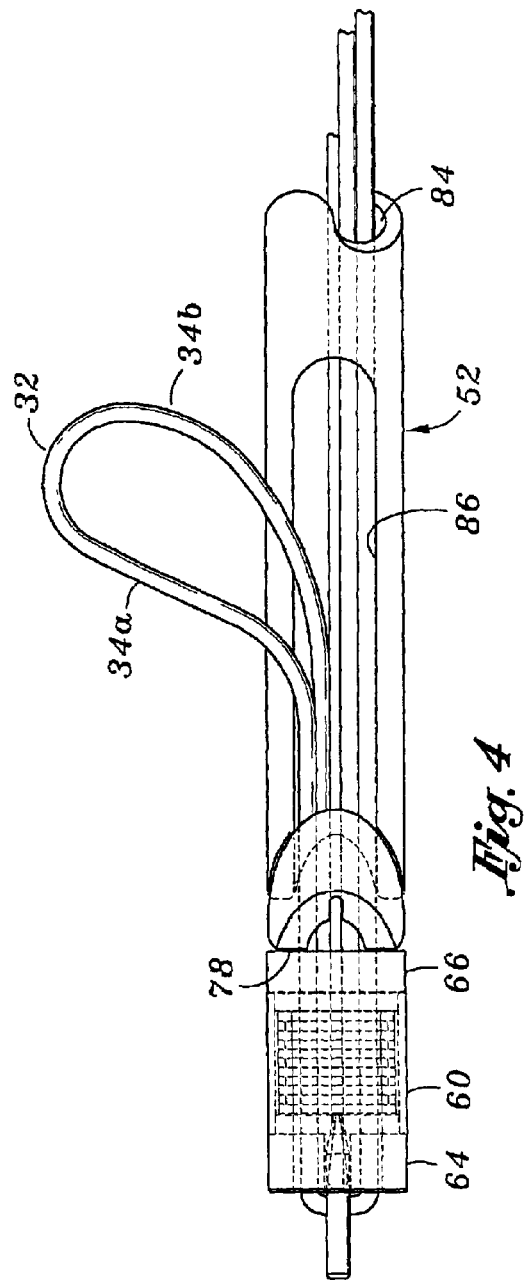

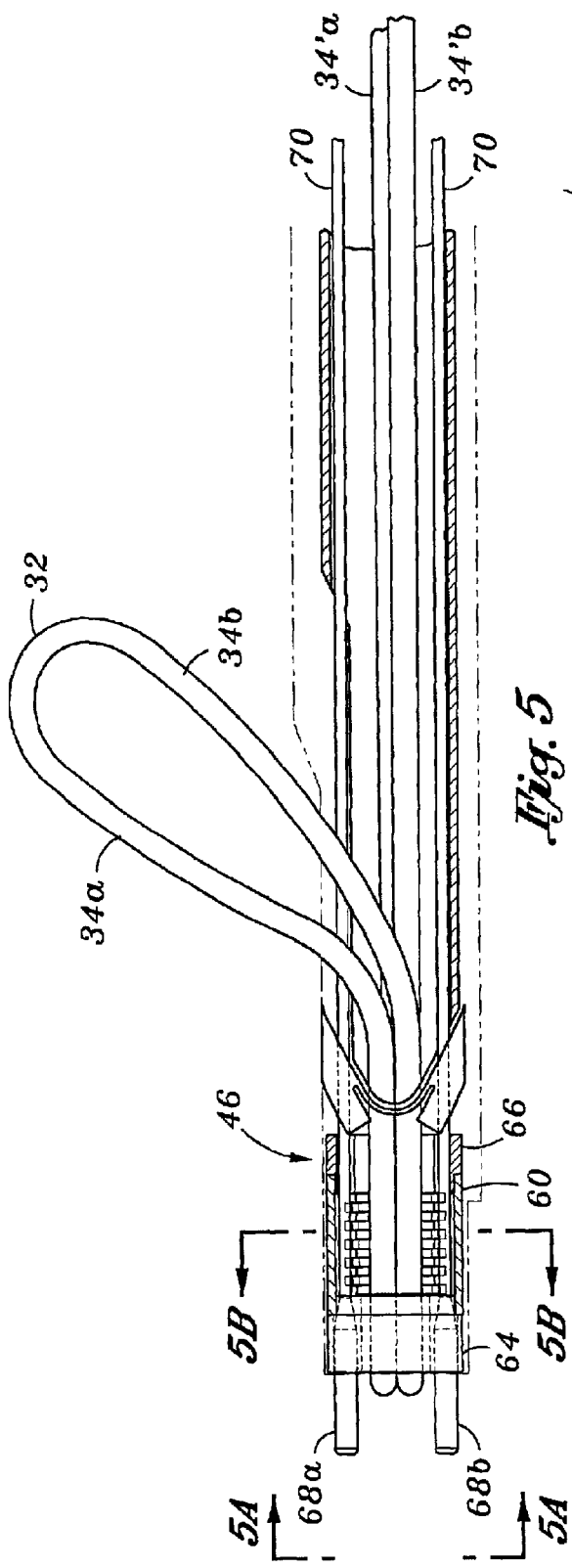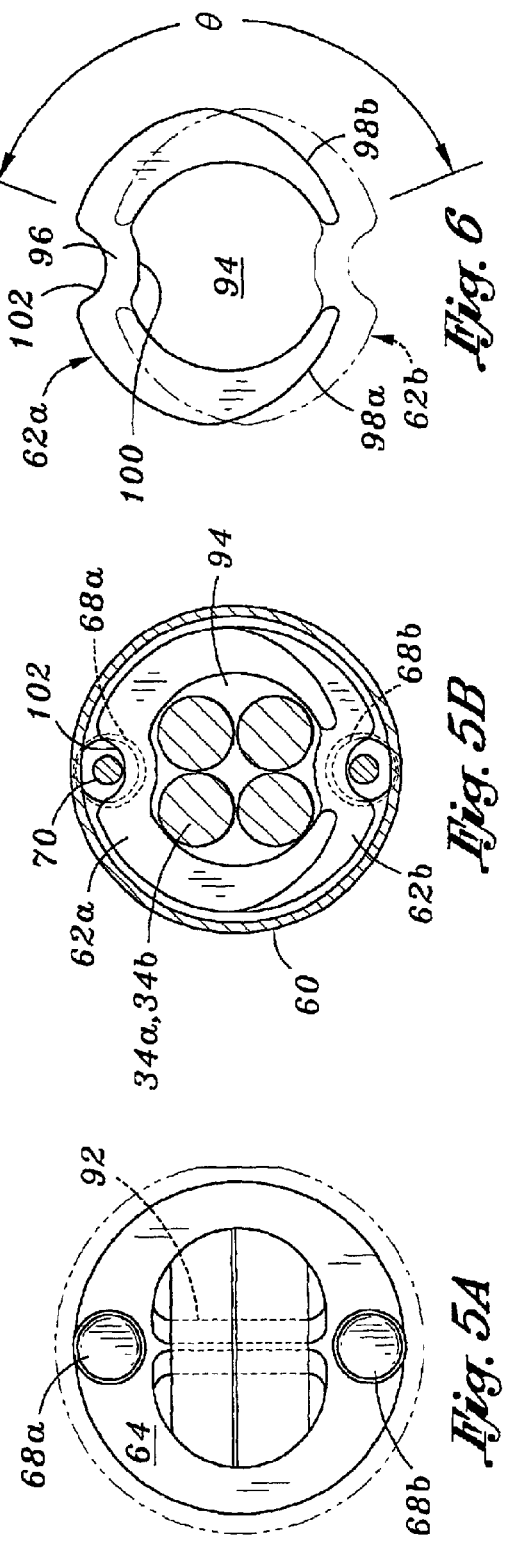

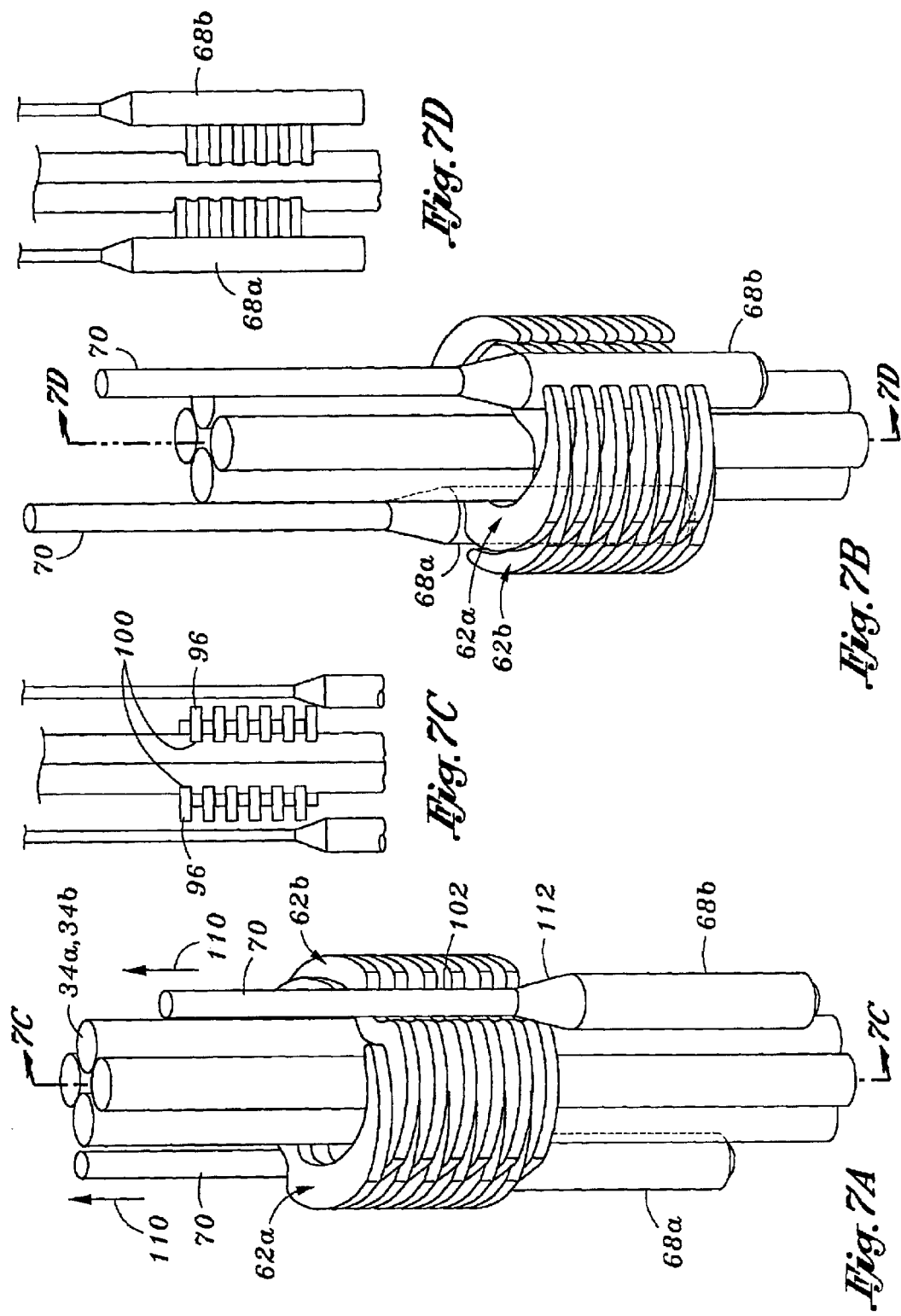

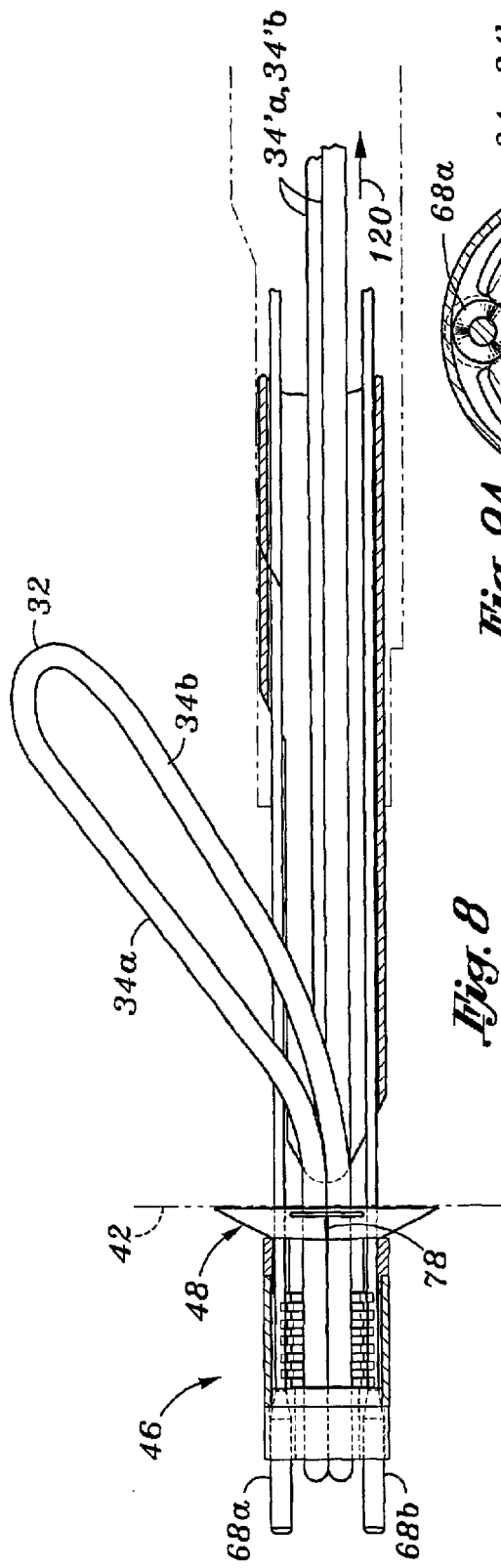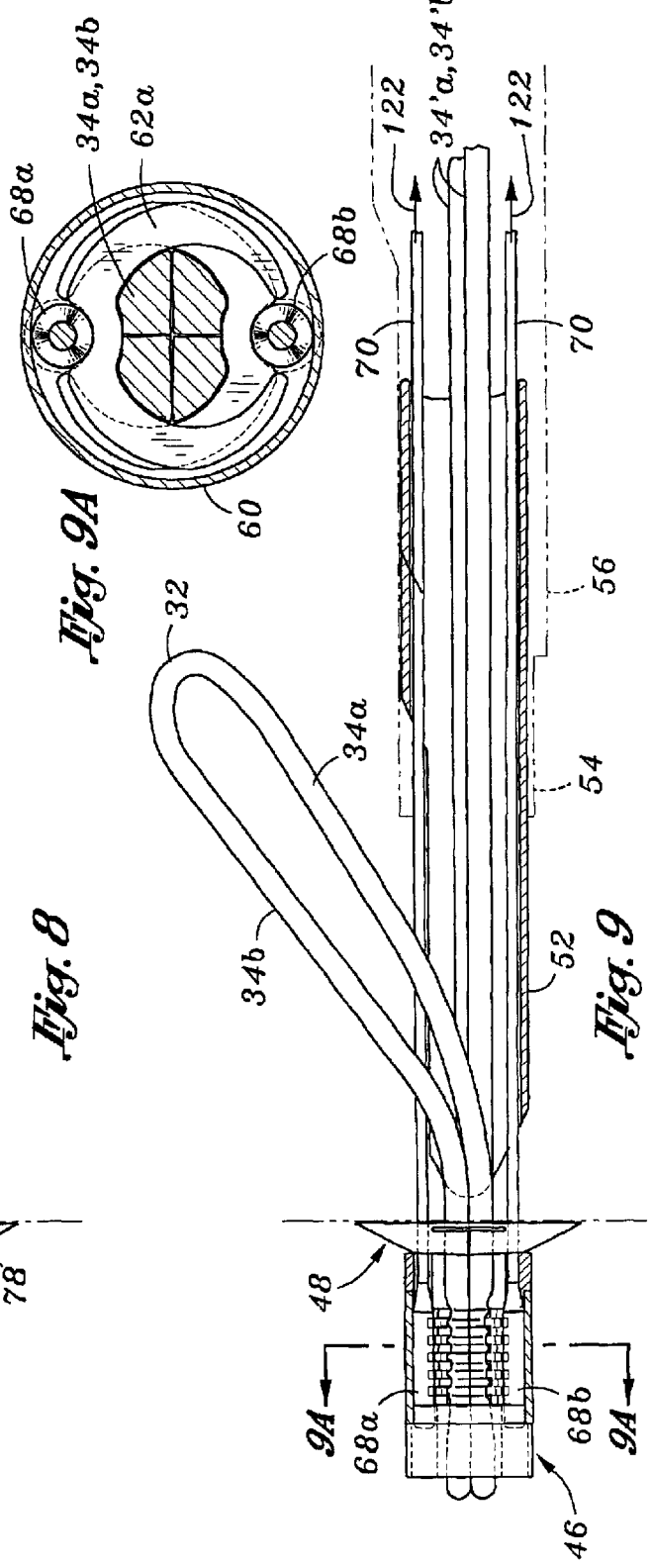

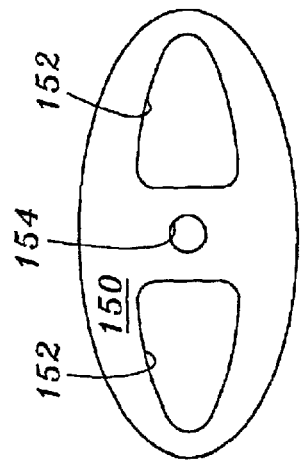
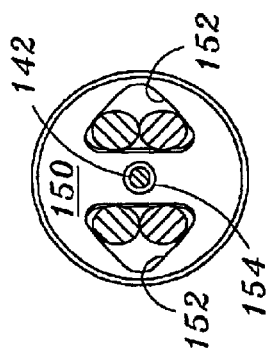
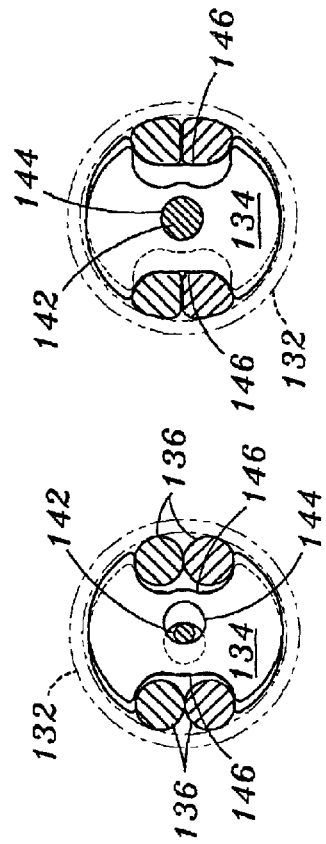
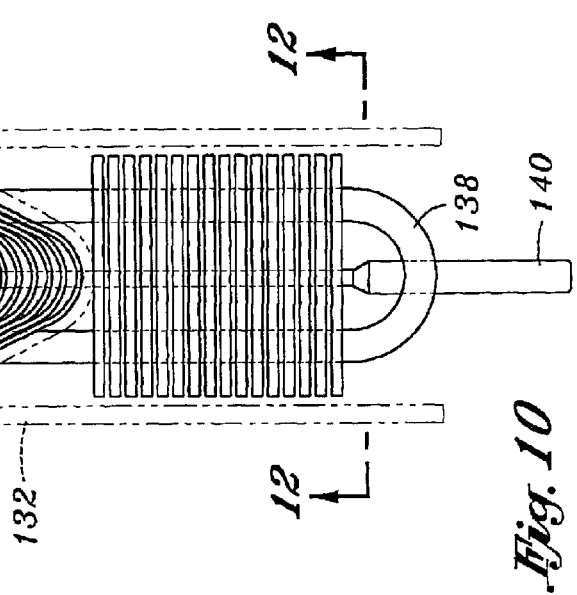

METHOD AND APPARATUS FOR ATTACHING CONNECTIVE TISSUES TO BONE USING A KNOTLESS SUTURE ANCHORING DEVICE

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

Today, the typical method for repairing a torn rotator cuff is surgical, through a large incision. This approach is presently taken in almost 99% of rotator cuff repair cases. There are two types of open surgical approaches for repair of the rotator cuff, one known as the "classic open" and the other as the "mini-open".

The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the so-called "transosseous tunnels", are "punched" through the bone or suture anchors are inserted. Following the suturing of the rotator cuff to the humeral head, the split deltoid is surgically repaired.

Although the above described surgical techniques are the current standard of care for rotator cuff repair, they are associated with a great deal of patient discomfort and a lengthy recovery time, ranging from at least four months to one year or more. It is the above-described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels, which are difficult or impossible to create arthroscopically using current techniques, the repair is completed by tying the cuff down against bone using the anchor and suture. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it can be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed. Consequently, because of the technical difficulty of the procedure, presently less than 1% of all rotator cuff procedures is of the arthroscopic type, and is considered investigational in nature.

Other difficulties with arthroscopic rotator cuff repair techniques are shortcomings related to currently available suture anchors. Suture eyelets in bone anchors available today, which, like the eye of a needle, are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment into the cancellous bone, the anchor is rotated 90° so that the long axis is aligned perpendicularly to the axis of the hole. The suture is pulled, and the anchor is seated up against the inside surface of the cortical layer of bone. Due to the mismatch in the dimensions of the long axis of the anchor and the diameter of the hole, the anchor cannot be retracted proximally from the hole, thus providing resistance to pull-out. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians' reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

As previously discussed, any of the anchor points for sutures mentioned above require that a length of suture be passed through an eyelet fashioned in the anchor and then looped through the soft tissues and tied down to complete the securement. Much skill is required, however, to both place the sutures in the soft tissues, and to tie knots while working through a trocar under endoscopic visualization.

There have been attempts to solve some of the problems that exist in current anchor designs. One such approach is disclosed in U.S. Pat. No. 5,324,308 to Pierce. In this patent, there is disclosed a suture anchor that incorporates both proximal and distal wedge blocks each having inclined mating faces. The distal wedge block has two suture thread holes at its base through which a length of suture may be threaded. The assembly may be placed in a drilled hole in the bone, and when tension is placed on the suture, the distal wedge block is caused to ride up against the proximal wedge block, expanding the projected area within the drilled hole, and locking the anchor into the bone. This approach is a useful method for creating an anchor point for the suture, but does not in any way address the problem of tying knots in the suture to fix the soft tissue to the bone.

The problem of placing sutures in soft tissues and tying knots in an endoscopic environment is well known, and there have been attempts to address the problem and to simplify the process of suture fixation. One such approach is disclosed in U.S. Pat. No. 5,383,905 to Golds, et al. The patent describes a device for securing a suture loop about bodily tissue that includes a bead member having a longitudinal bore and an anchor member adapted to be slidably inserted within the bore of the bead member. The anchor member includes at least two axial compressible sections, which define a passageway to receive two end portions of a suture loop. The axial sections collapse radially inwardly upon insertion of the anchor member within the bore of the bead member to securely wedge the suture end portions received within the passageway.

Although the Golds et al. patent approach utilizes a wedge-shaped member to lock the sutures in place, the suture legs are passing through the bore of the bead only one time, in a proximal to distal direction, and are locked by the collapsing of the wedge, which creates interference on the longitudinal bore of the anchor member. Also, no provision is made in this design for attachment of sutures to bone. The design is primarily suited for locking a suture loop, such as is used for ligation or approximation of soft tissues.

An approach that includes bone attachment is described in U.S. Pat. No. 5,584,835 to Greenfield. In this patent, a two-part device for attaching soft tissue to bone is shown. A bone anchor portion is screwed into a hole in the bone, and is disposed to accept a plug that has been adapted to receive sutures. In one embodiment, the suture plug is configured so that when it is forced into its receptacle in the bone anchor portion, sutures that have been passed through an eyelet in the plug are trapped by friction between the wall of the anchor portion and the body of the plug portion.

Although there is some merit to this approach for eliminating the need for knots in the attachment of sutures to bone, there exists a problem with not being able to properly set the tension in the sutures. The user is required to pull on the sutures until appropriate tension is achieved, and then to set the plug portion into the bone anchor portion. This action increases the tension in the sutures, and may garrot the soft tissues or increase the tension in the sutures beyond the tensile strength of the material, causing the sutures to break. In addition, the minimal surface area provided by this anchor design for pinching or locking the sutures in place will abrade or damage the suture so that the suture's ability to resist load will be greatly compromised.

A disclosure that incorporates bone attachment and eliminates knot tying is set forth in U.S. Pat. No. 5,702,397 to Goble et al. One embodiment, in particular, is shown in FIG. 23 of that patent and includes a bone anchor that has a threaded body with an inner cavity. The cavity is open to one end of the threaded body, and joins two lumens that run out to the other end of the threaded body. Within the cavity is disposed a gear, journaled on an axle. A length of suture is threaded through one lumen, around the gear, and out through the other lumen. A ball is disposed within the cavity to ride against a tapered race and ostensibly lock the suture in place. What is not clear from the patent disclosure is how the force D shown as the tension in the suture would lock the ball into the race. Although this embodiment purports to be a self-locking anchor adapted for use in blind holes for fixing sutures into bone, the construct shown is complicated, and does not appear to be adequate to reliably fixate the suture.

What is needed, therefore, is a new approach for repairing the rotator cuff or fixing other soft tissues to bone, wherein: suture tension can be adjusted and possibly measured, the suture anchor resides completely below the cortical bone surface, there is no requirement for the surgeon to tie a knot to attach the suture to the bone anchor, and wherein the procedure associated with the new approach is better for the patient, saves time, is uncomplicated to use, and easily taught to practitioners having skill in the art.

SUMMARY OF THE INVENTION

The present invention solves the problems outlined above by providing innovative bone anchor and connective techniques which permit a suture attachment which lies entirely beneath the cortical bone surface. In the present state of the art, the sutures which are passed through the tissues to be attached to bone typically are threaded through a small eyelet incorporated into the head of the anchor and then secured by tying knots in the sutures. Endoscopic knot tying is an arduous and technically demanding task. Therefore, the present invention discloses devices and methods for securing sutures to a bone anchor without the requirement of knot tying.

In accordance with one embodiment of the present invention, a knotless suture anchor apparatus for anchoring a length of suture with respect thereto is provided. The apparatus includes an anchor body having a proximal end, a distal end, and a lumen opening at the proximal end such that a length of suture may be introduced into the lumen from the proximal end. A plurality of suture-locking elements are located within the anchor body lumen and are each movable therewithin from respective first positions to second positions. When in their first positions the locking elements together define a generally uniform cross-section axial passage that is sized to permit axial movement of the length of suture therethrough. When displaced to their second positions, the cross-section of the axial passage converts to be irregular and therefore substantially restricts axial movement of the length of suture therethrough.

The axial passage may be located generally in the center of the lumen, wherein the suture-locking elements each move toward the center of the lumen from their first to their second positions. In a preferred embodiment, the suture-locking elements are substantially C-shaped and each surrounds and defines approximately three-quarters of the axial passage. At least one of suture-locking elements desirably moves in a different direction than the others from their respective first to their second positions. There are preferably at least four suture-locking elements that are stacked axially and arranged to move radially within the lumen, and wherein adjacent suture-locking elements move in opposite directions. A pair of suture-locking plugs may be provided that contact different suture-locking elements. The locking plugs are axially displaceable within the lumen and cam the suture-locking elements in opposite directions from their first to their second positions.

In a further aspect of the present invention, a knotless suture anchor apparatus for anchoring a length of suture with respect to a body cavity comprises an anchor body and a plurality of suture-locking elements. The anchor body is sized to fit within the body cavity and has a proximal end, a distal end, and a lumen opening at the proximal end such that a length of suture may be introduced therein. The locking elements are radially movable within the lumen of the anchor body from respective first positions to second positions. In their first positions, the locking elements together define a least one axial passage sized to permit axial movement of the length of suture therethrough. In their second positions, the locking elements reduce the size of the passage so as to clamp the length of suture therein and substantially restrict axial movement of the length of suture therethrough.

Preferably, the axial passage is centered in the lumen and the suture-locking elements each move radially toward the center of the lumen from their first to their second positions. The locking elements may be C-shaped, each surrounding approximately three-quarters of the axial passage. Desirably, at least one of the suture-locking elements moves in a different direction than the others. Furthermore, a pair of suture-locking plugs may be provided that, when axially displaced within the lumen, contact different suture-locking elements and move them in different directions. Each suture-locking plug has a first cross-sectional size and is attached to an actuation rod having a smaller cross-section, the actuation rod extending through the anchor body and to a proximal end of the apparatus to permit external manipulation of the suture-locking plug. The actuation rod may be separated from the suture-locking plug at a point of tensile weakness.

Alternatively, each suture-locking element has an aperture that is offset from the center of the lumen and at least one cavity around an external edge. Alternating suture-locking elements have apertures that are offset in opposite directions and partially aligned to permit passage of the smaller sized actuation rod. The length of suture passes between the cavities and the inner wall of the anchor body. Axially displacing the actuation rod pulls the larger locking plug into the partially aligned apertures so as to radially displace the locking elements and clamp the length of suture against the inner wall of the anchor body.

In accordance with a further aspect of the invention, a method of securing soft tissue with respect to a body cavity without knots is provided. The method includes a step of passing a length of suture through soft tissue so that a loop of suture material is embedded in the soft tissue resulting in two free ends. An anchor body is provided having an open proximal end and a lumen. A plurality of suture-locking elements located within the anchor body lumen are each movable within the lumen from respective first positions to second positions. In their first positions, the locking elements together define a generally uniform cross-section axial passage sized to permit axial movement of the length of suture therethrough. In their second positions, the locking elements convert the cross-section portion of the axial passage to be irregular and therefore substantially restrict axial movement of the length of suture therethrough. The method includes passing the two free ends of the length of suture into the lumen of the anchor body through the open proximal end and through the passage with the suture-locking elements in their first positions. The two free ends extend out of the lumen through the open proximal end. The anchor body is fixed with respect to a body cavity, and the loop of suture material is tightened by pulling on one or both of the two free ends of the length of suture. Finally, two free ends of the length of suture are fastened with respect to the anchor body without knots by displacing the suture-locking elements to their second positions.

The soft tissue may be a tendon, and the body cavity is formed in a bone. More particularly, the tendon is the rotator cuff tendon, and the bone is the humeral head.

The method may further include providing a suture-locking plug that is axially displaceable within the lumen so as to contact at least some of the suture-locking elements and move them from their first to their second positions. Desirably, at least one of the suture-locking elements moves in the opposite direction to the others from their first to their second positions, and the method includes axial displacement of the suture-locking plug to move the suture-locking elements in opposite directions.

The present invention also provides a method of securing soft tissue with respect to a body cavity without knots. The method includes passing a length of suture through soft tissue so that a loop of suture material is embedded in the soft tissue resulting in two free ends. An anchor body having an open proximal end and a lumen is provided. The two free ends of length of suture are passed into a generally axially uniform passage in the lumen of the anchor body through the open proximal end and wrapped around a pulley at a distal end. The two free ends extend through the passage and back out of lumen through the open proximal end such that there are four strands within the anchor body. The anchor body is fixed with respect to a body cavity, and the loop of suture material is tightened by pulling one or both of the two free ends of the length of suture that extend out of the proximal end of the anchor body. Finally, the two free ends of the length of suture are fastened with respect to the anchor body without knots by displacing a series of suture-locking elements within the anchor body to reduce the size of the passage and desirably convert it from uniform to irregular.

In the described method, the soft tissue may be a tendon and the body cavity may be formed in bone. In a particular preferred operation, the tendon is the rotator cuff tendon, and the bone is the humeral head. The step of fixing the anchor body with respect to the body cavity may include forming a body cavity, passing the anchor body therein, and radially extending an anchoring member. In a preferred embodiment, the anchoring member is located adjacent a proximal end of the anchor body and interferes with the cortical layer of the bone to prevent proximal removal of the anchor body from the cavity. The method may include providing a suture-locking plug movable within the lumen from a first position to a second position that causes displacement of the locking elements and compression of the two free ends of the length of suture. A proximal actuation rod that extends out of the lumen from the proximal end of the anchor body may be coupled to the suture-locking plug, wherein the method includes displacing the actuation rod in the proximal direction with respect to the anchor body, and desirably severing the actuation rod from the suture-locking plug after the step of compressing the suture.

Now, it is to be understood that the above described invention is particularly suited to locking sutures that have been passed through soft tissues and are to be anchored to bone. The creation of an anchor point within the bone is outside the scope of this invention, although many alternative methods of anchoring suture to bone are contemplated. For example, some currently preferred methods are discussed in U.S. patent application Ser. No. 09/616,802, entitled Method & Apparatus for Attaching Connective Tissues to Bone Using a Suture Anchoring Device, filed on Jul. 14, 2000, and U.S. patent application Ser. No. 09/876,260, entitled Method & Apparatus for Attaching Connective Tissues to Bone Using a Cortical Bone Anchoring Device, filed on Jun. 6, 2001. The referenced applications are commonly assigned with the present application, and are expressly incorporated by reference in their entirety herein. Other prior art anchors, such as screws, moly bolts, and pop rivets may be adapted for use with the present invention as well.

The invention, together with additional features and advantages thereof, may best be understood by reference to the following description taken in conjunction with the accompanying illustrative drawing.

BRIEF DESCRIPTION OF THE DRAWINGS

FIG. 1A is a partial sectional view through the left shoulder of a human as seen from the front showing the use of a minimally invasive soft tissue to bone attachment system, or suture anchor system, of the present invention;

FIG. 1B is an enlarged sectional view taken within the circle denoted 1B in FIG. 1A;

FIGS. 1C–1F are enlarged sectional views of several steps in the use of the suture anchor system of FIG. 1A to reattach a rotator cuff tendon;

FIG. 2 is a perspective exploded view of a combined suture-locking portion and bone anchor structure in a distal end of an exemplary suture anchor system of the present invention;

FIG. 3 is a partially assembled elevational view of the distal end of the suture anchor system of FIG. 2;

FIG. 4 is a plan view of the distal end of the suture anchor system of FIG. 2 in an assembled state, ready for use in the operational step of FIG. 1B;

FIG. 5 is a partial longitudinal sectional view as seen in elevation of the distal end of the assembled suture anchor system of FIG. 4;

FIG. 5A is an end elevational view of the suture locking portion of the system of FIG. 5 taken along line 5A—5A;

FIG. 5B is a transverse sectional view of the suture locking portion of the system of FIG. 5 taken along line 5B—5B, showing movable suture-locking elements disposed within an anchor body;

FIG. 6 is an end elevational view of two of the suture-locking elements seen in FIG. 5B isolated to better illustrate their cooperative shapes;

FIG. 7A is a perspective view of several internal components of the suture locking portion of the system of FIG. 2, specifically illustrating a pair of suture-locking plugs arranged for axial movement to the outside of a plurality of inter-engaging suture-locking elements shown in first positions, and four strands of suture slidable within a lumen defined by the suture-locking elements when in their first positions;

FIG. 7B is a perspective view of the suture-locking portion components of FIG. 7A after axial displacement of the suture-locking plugs which forces the suture-locking elements into second positions, thus reducing the size of the lumen defined therein and clamping the strands of suture;

FIGS. 7C and 7D are longitudinal sectional views of the suture locking portion of the system of FIG. 2 taken along the corresponding section lines in FIGS. 7A and 7B;

FIG. 8 is a partial longitudinal sectional view of the assembled suture anchor system similar to FIG. 5, and illustrates deployment of a bone anchoring member and tightening of the strands of suture within the system; the figure also illustrates the suture-locking plugs and elements in their positions as shown in FIG. 7A;

FIG. 9 is a view similar to FIG. 8 after axial displacement of the suture-locking plugs have forced the suture-locking elements into their second positions, as was seen in FIG. 7B, thus clamping the strands of suture therein;

FIG. 9A is a transverse sectional view through the suture-locking portion of the system of FIG. 9 taken along line 9A—9A;

FIG. 10 is a partial longitudinal sectional view through an alternative suture-locking portion and bone anchor structure in a distal end of an exemplary soft tissue to bone attachment system of the present invention;

FIG. 11A is an end elevational view of the bone anchor structure of FIG. 10 taken along line 11—11;

FIG. 11B is a plan view of a single bone anchor member of the bone anchor structure seen in FIG. 10;

FIGS. 12A and 12B are transverse sectional views through the alternative suture-locking portion seen in FIG. 10 and taken along line 12—12, respectively illustrating suture-locking elements in their first or undeployed positions and their second or deployed positions.

DESCRIPTION OF THE PREFERRED EMBODIMENT

Figure 1D:
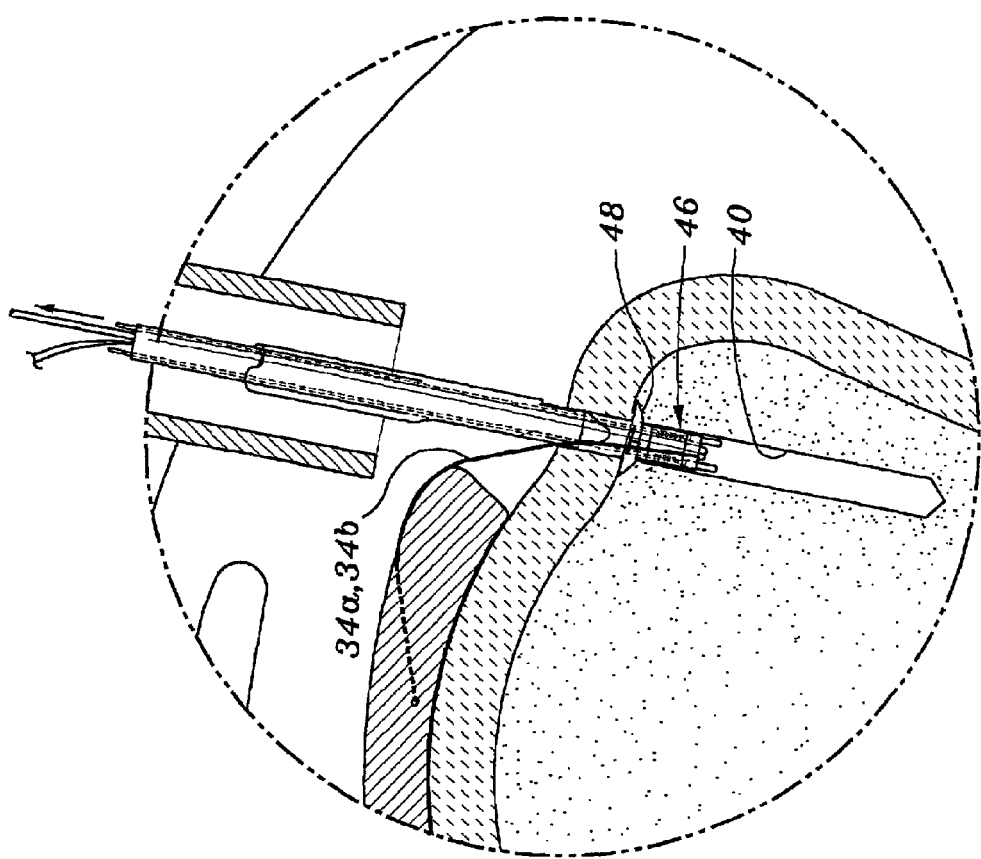

The present invention provides an improved knotless suture anchor apparatus for anchoring a length of suture with respect to a body cavity. In the exemplary embodiment described herein, the apparatus is used to anchor a length of suture to a bone structure, specifically the humeral bone of the human shoulder. The length of suture is desirably looped through soft tissue, such as a rotator cuff tendon, to approximate and fix the soft tissue with respect to the body cavity (e.g., bone structure). It should be understood, however, that the suture anchor apparatus may be utilized to secure a length of suture to body cavities other than in a bone structure, and may even be used to anchor the suture outside of a body cavity, or merely to a predetermined location within the body. In this regard, the preferred apparatus includes an anchor body within which the length of suture may be anchored without knots. If the anchor body is to be implanted within the body cavity, structure on its exterior or coupled therewith may also be provided for securing the anchor body therein. In a preferred embodiment, the anchor body is positioned within a pre-formed cylindrical cavity in a bone structure, and a bone anchor is deployed at one end of the anchor body to hold it within the cavity.

As mentioned, the present invention is particularly well-suited for repairing rotator cuff injuries by re-attaching the rotator cuff tendon to the outside of the humeral head. The invention permits minimally invasive surgeries on such injuries and greatly facilitates rapid and secure fixation of the rotator cuff tendon to the humeral head. It should be understood that the same principles described herein apply to the repair of other injuries in which soft tissue is to be re-attached to a bone structure.

FIGS. 1A–1F are cross-sectional views through the left shoulder of a human as viewed from the front and illustrate the use of an exemplary soft tissue to bone attachment system, or suture anchor system 20, for repairing a rotator cuff tendon injury. The rotator cuff tendon 22 is shown in its natural position overlying the bulbous humeral head 24 of the humerus bone 26. In rotator cuff injuries, the tendon 22 partially or completely separates from its attachment point to the humeral head 24, which point of attachment is typically located along an angled shelf, the greater tuberosity 28. In minimally invasive surgeries to repair the rotator cuff injury, the surgeon threads one or more sutures through the rotator cuff tendon 22 and anchors them to the greater tuberosity 28. The suture anchor system 20 of the present invention facilitates this latter step of anchoring the sutures to the greater tuberosity 28.

With reference first to FIG. 1A, a generally tubular trocar 30 provides a conduit through the soft tissue of the shoulder for passage of the suture anchor system 20 of the present invention. Per convention, the trocar has a proximal end outside of the patient that the surgeon manipulates, and a distal probe or end that enters the body and through which the surgery is performed. Typically, the surgeon makes an incision or stab wound through the outer dermal layers of sufficient size to permit passage of the trocar 30 through the skin and the deltoid muscle, into proximity with the humeral head 24. Various trocars and techniques for creating the approach passageway are known and may be utilized with the present invention. In addition, more than one incision and conduit may be necessary to perform the several suturing and anchoring steps.

After establishing one or more direct conduits to the humeral head 24, the surgeon passes a length of suture through the soft tissue of the rotator cuff tendon 22 so that a loop 32 of suture material is embedded therein, as seen in FIG. 1B. The two free ends 34a, 34b of the length of suture are withdrawn from the patient and coupled to the suture anchor system 20. The specifics of this coupling and subsequent manipulation of the two free ends of the suture will be described more fully below. For the purpose of explaining the exemplary method of use, it is sufficient to understand that the two free ends 34a, 34b pass into a lumen at the distal end of the suture anchor system 20 and, after being looped around suture anchoring structure, extend through the lumen in a proximal direction to a proximal end of the system to enable fixation or pulling of the suture ends. Therefore, the two free ends 34a, 34b are shown at the top of FIG. 1B projecting from a proximal end of the system 20. The system 20 further includes a plurality of concentrically disposed cannulas or tubes as shown that perform the knotless suture anchoring operation. The interrelationship and functioning of these tubes will also be more fully explained below.

Figure 1C:
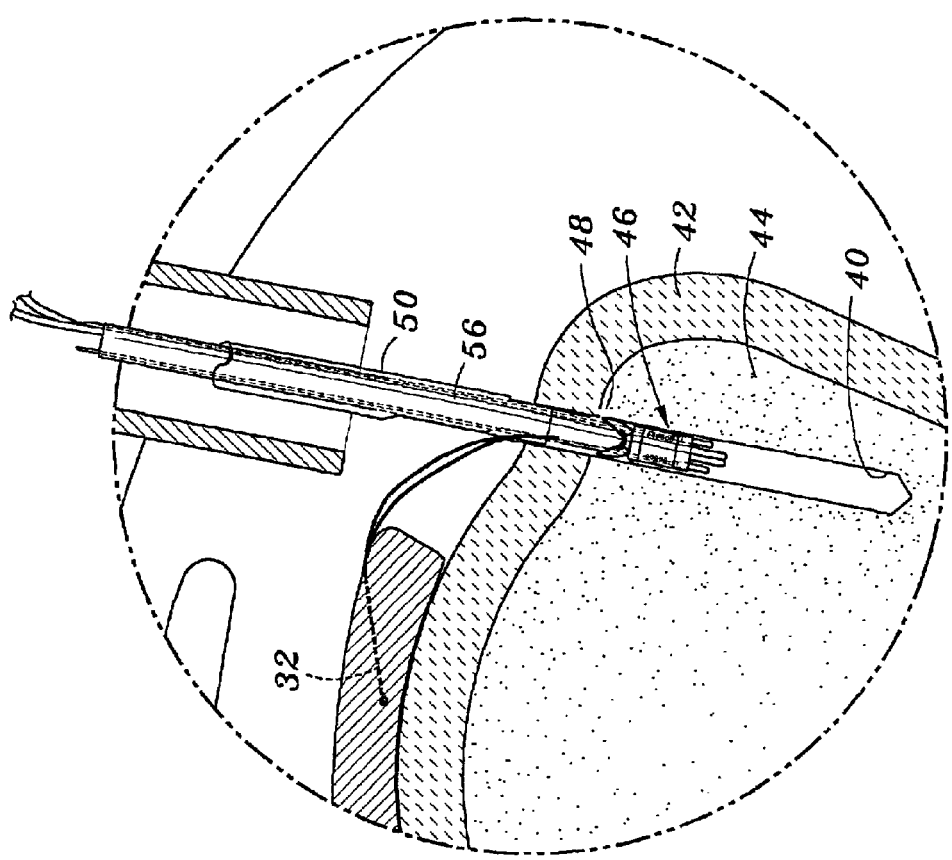

The exemplary suture anchor system 20 as illustrated is particularly suitable for anchoring a suture to a body cavity, specifically the humeral head 24 as shown. When anchoring sutures to such a bone structure, a conventional technique is to first form a blind hole or cavity 40 through the cortical layer 42 and into the soft cancellous matter 44, as seen in FIGS. 1B and 1C. The surgeon then positions a suture anchor 46 within the cavity 40 and secures it therein to prevent removal from the cavity.

The suture anchor 46 performs two functions: anchoring itself within the body cavity and anchoring the sutures therein. In the embodiment as illustrated in FIGS. 1C and 1D, the former function is accomplished using an expandable anchoring member 48 located at the proximal end of the suture anchor 46. The anchoring member 48 functions like a toggle bolt used in ceiling fixtures, and specifically expands to a larger dimension in the cavity 40 beyond the hard cortical bone 42. FIG. 1D shows the anchoring member 48 after having been radially expanded from proximal movement of the suture anchor 46 (compare to the axial location of the suture anchor in FIG. 1C). In this manner, the suture anchor 46 is prevented from being removed from the cavity 40 once the anchoring member 48 is deployed.

The present invention illustrates a particular anchoring member 48, although any similar expedient will work. For example, a different toggle-like anchoring member may be used such as shown in co-pending application Ser. No. 09/876,488 filed on Mar. 2, 2001, expressly incorporated by reference herein. Alternatively, an anchoring structure that expands into contact with the cancellous matter 44 or a body resembling a screw may also be used. In short, the present invention is not considered to be limited by the particular anchoring structure that secures the suture locking portion to the bone or other body cavity.

The second function of the suture anchor 46 is the anchoring or fixation of the suture with respect to the suture anchor itself, without the use of knots. Desirably, the particular manner of anchoring the suture with respect to the suture anchor 46 permits easy adjustment of the length of suture between the suture anchor 46 and the loop 32 formed in the soft tissue prior to anchoring the suture. This adjustment allows the surgeon to establish the proper tension in the length of suture for effective repair of the soft tissue, and reattachment of the rotator cuff tendon 22 in the illustrated embodiment. So, for example, FIG. 1D also illustrates the two free ends 34a, 34b of the length of suture having been pulled taught prior to securing within the suture anchor 46 (see comparison with FIG. 1C).

FIG. 1E shows the fully deployed suture anchor 46 after the free ends 34a, 34b have been placed in tension and locked within the suture anchor. The step of locking the length of suture within the suture anchor 46 is desirably accomplished by proximal displacement of a pair of suture-locking plugs, which are connected to actuation rods or pull wires. The movement arrows 49 indicate this displacement, and the specifics of the locking structure will become clear below. Importantly, and as also explained below, the present invention enables the length of suture to be anchored without altering the proper tension.

Although not shown, the remaining steps in the procedure involve withdrawing the concentric tubes from the surgical site as seen in FIG. 1F and severing the free ends 34a', 34b' close to the suture anchor 46. It should be noted that no portion of the suture anchor 46 or sutures 34a', 34b' projects above the outer surface of the humeral head 24, and in addition no knots are left to irritate the patient.

FIGS. 1–6 are various views illustrating a distal end of the exemplary suture anchor system 20 of the present invention. The several components of the system are seen exploded in FIG. 2 and can be grouped as the suture anchor 46, the bone anchoring member 48, and a delivery system 50. For purpose of orientation, the right side will be referenced as the proximal side and the left side as the distal side. Prior to a detailed discussion of the suture anchor 46 and anchoring member 48, several concentrically disposed tubes comprising the delivery system 50 will be described.

An inner delivery tube 52 slides within an introducer tube 56 that has a shoulder 54. The introducer tube 56 may include a valve (not shown) on a proximal end to prevent fluid leakage therefrom. Alternatively, such a fluid leakage valve may be provided on the proximal end of the trocar 30 seen in FIG. 1A. The concentric tubes 52, 56 of the suture anchor system 20 are relatively axially movable to deploy the suture anchor 46. Various means are known to relatively displace concentric tubes a predetermined distance and/or with a predetermined displacement force. For example, the concentric tubes may extend out of the trocar 30 to an actuation device in the form of concentric syringe bodies/finger tabs. Alternatively, the concentric tubes may be attached to relatively movable parts in a gun-type handle, and actuated by triggers or other such levers. It is to be understood therefore that the present invention is not limited by the particular actuation device on its proximal end, and no further description in this regard will be provided.

The suture anchor 46 includes a generally tubular anchor body 60, two series of suture-locking elements 62a, 62b, a distal end cap 64, a proximal end cap 66, and a pair of suture-locking plugs 68a, 68b. As seen, each of the suture-locking plugs 68a, 68b has an actuation rod 70 removably attached to a proximal end, that extends proximally within the delivery tube 52 and eventually projects from the proximal end of the suture anchor system 20, as seen in FIG. 1E.

The components of the suture anchor 46 are shown assembled in FIG. 3, and again in FIG. 4 as assembled with the other components of the suture anchor system 20. The end caps 64, 66 have stepped extensions that fit closely within the inner diameter of the tubular anchor body 60 such that the outer surfaces of these three elements define a smooth outer cylinder. The thus assembled anchor body 60 and end caps 64, 66 define a tube having a lumen (not numbered) opening at proximal and distal ends. The end caps 64, 66 axially retain the suture-locking elements 62a, 62b within the anchor body 60. As will be described below, these elements 62a, 62b cooperate to secure a length of suture within the anchor 46 by relative radial movement, and are stacked closely yet with negligible compression so as to enable relative movement. The close stacking of these elements 62a, 62b and presence of the end caps 64, 66 prevent relative axial movement therebetween. As seen in FIG. 2, two diametrically opposed bores 71 in the distal end cap 64 receive and align the locking plugs 68, while two smaller diametrically opposed bores 73 in the proximal end cap 66 receive and align the actuation rods 70.

The bone anchoring member 48 is seen in perspective in FIG. 2, and in elevation in FIG. 3. As mentioned above, the tubular anchoring member 48 is exemplary only, and other structures may be utilized. For instance, the anchoring member 48 illustrated is a separate element disconnected from the suture anchor 46. Alternatively, an anchoring member that is formed integrally with, or connected to, the suture anchor 46 may be used.

The bone anchoring member 48 includes a pair of wings 72a, 72b that are connected by a pair of deformable strips 74. The wings 72a, 72b are shown in their undeployed, unexpanded states in FIGS. 2 and 3, wherein they, along with the strips 74, define something of a U-shape in elevation. As will be seen below, in particular with reference to FIG. 8, the wings 72a, 72b are ultimately deployed outwardly with respect to each other such that the strips 74 assume a relatively linear shape, aligned with a proximal surface of the wings. This outward deployment is indicated by the arrows 76 in FIG. 3. A pair of stop surfaces 78 ultimately contact and limit this outward deployment, as seen in FIG. 8.

The exemplary bone anchoring member 48 is located between the suture anchor 46 and the delivery tube 52. In the undeployed state, as seen in FIGS. 3 and 4, the U-shaped proximal surface of the member 48 conforms and is rotationally fixed with respect to a blunt distal tip 80 of the delivery tube 52. As seen in FIG. 4, corners of the distal stop surfaces 78 contact the proximal end cap 66 of the suture anchor 46. The bone anchoring member 48 defines a lumen 82 therethrough, as seen in FIG. 2. The actuation rods 70 pass through the hollow suture anchor 46, through the lumen 82, and through a passage 84 in the delivery tube 52, to the proximal end of the trocar 30 (FIG. 1A). As will be clear shortly, tension on the actuation rods 70 maintains the suture anchor 46 and bone anchoring member 48 together and held against the blunt distal tip 80 of the delivery tube 52, as in FIG. 4. Even after removal of the delivery tube 52 and actuation rods 70, as seen in FIG. 1F, the suture anchor 46 and bone anchoring member 48 remain held together under the tension of the two free ends 34a, 34b of the length of suture.

FIG. 4 shows the suture loop 32 extending transversely from within an axial slot 86 of the delivery tube 52. As seen in FIG. 2, both the intermediate tube 54 and introducer tube 56 are also provided with axial slots 88, 90, respectively. The slots 86, 88, 90 align and permit lateral passage of the two free ends 34a, 34b of the length of suture into the passage 84 in the delivery tube 52, and from there through the bone anchoring member lumen 82 and into the suture anchor lumen to be anchored.

Now, referring back to FIG. 1B, there is shown the entrance of the two free ends 34a, 34b of the length of suture into the aligned slots in the suture anchor system 20. The loop 32 is first embedded in the rotator cuff tendon 22 and then the two free ends 34a, 34b can be withdrawn from the body and inserted into the system 20. The suture anchor 46 is then fixed in the humeral head 24 and the suture anchored therewithin. The aligned slots 86, 88, 90 (FIG. 2) in the system 20 allow the concentric tubes 52, 54, 56 to help in securing the rotator cuff tendon 22 to the humeral head 24 and then be easily removed.

With reference now to FIG. 5, the two free ends 34a, 34b of the length of suture pass in a distal direction through the bone-anchoring member lumen 82 and into the lumen of the suture anchor 46. The two ends 34a, 34b pass completely through the suture anchor 46 and loop around a cross member 92 in the distal end cap 64 (see FIGS. 2 and 5A). After looping around the cross member 92, the free ends 34a, 34b return in a proximal direction back through the lumen of the suture anchor 46 and the bone anchoring member lumen 82. Within the lumen of the suture anchor 46 there are four separate strands of the two free ends 34a, 34b of the length of suture, as can be seen in the cross-section of FIG. 5B. At the location of the aligned slots 86, 88, 90, the four strands separate and the two free ends 34a', 34b' continue in a proximal direction to the proximal end of the system 20.

The structure and function of the suture-locking elements 62a, 62b will now be described with reference to FIGS. 5, 6, 7A, and 7B. FIG. 5B shows the shape of one of the first series of suture-locking elements 62a overlying one of the second series of suture-locking elements 62b, and both surrounding the four strands of the two free ends 34a, 34b of the length of suture. The elements 62a, 62b are shown in their undeployed, first positions. The interior edges of the suture-locking elements 62a, 62b define a generally round passage 94 within which the strands of the length of suture are constrained. The passage 94 has a generally uniform axial cross-section, meaning that the majority of the cross-section of the internal passage is relatively smooth axially. Therefore, the shape of the passage 94 is generally as seen in FIGS. 5B and 6 along the entire axial stack of elements 62a, 62b.

There are advantageously more than four total elements 62a, 62b for a minimum of suture clamping, and preferably there are at least ten. With four elements 62, two on each side moving in opposite directions, adequate frictional interference with the length of suture is created. Of course, the greater number of elements 62 increases the frictional resistance to suture pull-through, and concurrently the clamping force can be reduced. Moreover, although alternating elements 62a, 62b moving 180° to each other are shown, more than two differently oriented elements can be used that move in different yet not necessarily opposite directions. For instance, three series of elements that move in directions that are oriented 120° with respect to each other can be used.

Each suture-locking element 62a, 62b is substantially C-shaped and surrounds and defines (at its level within the anchor body lumen) at least three-quarters of the axial passage 94. With reference to FIG. 6, each element 62a (and each element 62b) has a central bridge portion 96 and a pair of arcuate arms 98a, 98b. The passage 94 is defined by the inner edges of the bridge portion 96 and arms 98a, 98b, and the profile is generally round except for an inward bulge 100 at the bridge portion. Each of the arms 98a, 98b terminates at points that are spaced apart a distance corresponding to a circumferential arc around the passage 94 of less than 45°, and preferably about 30°.

The elements 62a, 62b in the two series are stacked in an alternating fashion, so that each element in the first series of elements 62a is surrounded by two elements in the second series of elements 62b, and visa versa (except, of course, for those on the stack ends). Moreover, the alternating elements 62a, 62b are oppositely oriented 180° about the axis such that the spaced-apart ends of each element 62a align with the inward bulge 100 at the bridge portion 96 of each adjacent element 62b. This can be seen in FIG. 6 at the top and bottom. Because there is a space between the ends of the arms 98a, 98b, a slight non-uniformity in the inner wall of the passage 94 is created. That is, there is a gap between each two adjacent bulges 100 of the first series of elements 62a. However, because the bulges 100 are relatively closely spaced and aligned, the passage 94 can still be considered generally uniform in axial cross-section. Indeed, FIG. 6 illustrates an arc θ on one side of the two series of elements 62a, 62b that corresponds to the portion of the passage 94 on that side that is entirely uniform (i.e., smooth) when the elements are in their first positions.

The outer edge of each of the first series of elements 62a is generally round, and in combination with the outer edges of the second series of elements 62b, defines a cylinder that fits closely within the tubular anchor body 60, as seen in FIG. 5B. Each of the elements 62a, 62b defines a substantially semi-circular cavity 102 in its outer edge at the location of the bridge portion 96. As seen in FIGS. 5B and 6, the cavities 102 in the first series of elements 62a are diametrically opposed from the cavities in the second series of elements 62b. The series of aligned cavities 102 on both sides of the suture anchor 46 creates tunnels through which an actuation rod 70 passes, when the suture anchor 46 is assembled, and prior to actuation thereof. This is seen in FIG. 5B which illustrates the relative sizes of the actuation rods 70 and the larger diameter suture-locking plugs 68a, 68b. With reference to FIG. 5, it will be noted that in the undeployed state the suture-locking plugs 68a, 68b are located just distal to the tubular anchor body 60 and enclosed suture-locking elements 62a, 62b.

FIGS. 7A and 7B show the suture-locking elements 62a, 62b and suture-locking plugs 68a, 68b isolated to better illustrate their interaction and the advantageous mechanism for anchoring one or more lengths of suture without knots. FIG. 7A shows the elements 62a, 62b in their undeployed relationship, as previously illustrated in FIGS. 5–6, while FIG. 7B shows the deployed state. FIG. 7C is a cross-section through the bridge portions 96 of each element 62a, 62b in their first positions.

Deployment involves axial movement of the suture-locking plugs 68a, 68b in the direction of arrows 110 which causes radial movement of the suture-locking elements 62a, 62b. Each suture-locking plug 68a, 68b has a proximal taper 112 that initially resides adjacent the distal-most suture-locking element 62a or 62b. Proximal movement in the direction of arrows 110 of the actuation rods 70 pulls the tapers 112 and then the suture-locking plugs 68a, 68b into the aligned series of cavities 102 defined on the outer edges of the suture-locking elements 62a, 62b. As can be seen from FIG. 5B, forcing the larger diameter suture-locking plugs 68a, 68b into the aligned cavities 102 in turn cams each of the suture-locking elements 62a, 62b radially inward. In particular, the first series of suture-locking elements 62a moves in an opposite direction to the second series of suture-locking elements 62b, both moving toward the center of the anchor body lumen.

Radially inward movement of the suture-locking elements 62a, 62b from first positions to second positions converts the cross-section of the axial passage 94 from generally uniform to irregular, and therefore substantially restricts axial movement of the lengths of suture 34a, 34b that are disposed therein. The irregularity can be seen in the cross-section of FIG. 7D and generally comprises alternating misaligned bulges 100 or "teeth" that compress the lengths of suture 34a, 34b from opposite sides. Because the bulges 100 are misaligned, the effect is an irregular compression of the lengths of suture 34a, 34b that creates significantly more frictional resistance to suture pull-through, than if the bulges were aligned.

Another way to state the clamping effect is that the suture-locking elements 62a, 62b are initially disposed in first positions that together define the axial passage 94 sized to permit axial movement of the lengths of suture 34a, 34b therethrough. Axial movement of the suture-locking plugs 68a, 68b into the tunnels created by the cavities 102 cams the elements 62a, 62b inward toward the center of the anchor body lumen into second positions that, taken as an aggregate, reduce the size of the passage 94. The reduced passage 94 clamps the lengths of suture 34a, 34b therein and substantially restricts their axial movement therethrough.

The suture-locking elements 62a, 62b are dimensioned to compress or "crush" the length of suture in the lumen 94 and interfere with its axial movement therethrough. The amount of interference may be measured by the amount of pull force necessary to move the suture once the elements 62a, 62b are in their second positions. Desirably, the pull force is in a range that would exceed the USP (United States Pharmacopeia) Standard knot pull strength (USP 24) of the suture used. In the specific case of #2 braided polyester suture, this knot pull strength is approximately 3.5 Kgf. In practice, however, the knot pull strength of commercially available #2 braided polyester sutures approaches 14 Kgf.

The particular structure and arrangement of the suture-locking elements 62a, 62b may differ from that shown. For instance, the elements may not be oriented in radial planes and be displaced radially, but instead may be angled and be displaced at an angle. Or, the elements may be arranged to rotate in one or more directions upon axial translation of the locking plugs 68a, 68b, thus creating the meshing teeth, so to speak, that grip the suture strands. Also, there may be only one series of elements that displace in one direction, thus crushing the suture strands against the inner wall of the tubular anchor body 60 or against a fixed structure within. Those of skill in the art will therefore understand that the elements 62a, 62b disclosed are exemplary only, and others are contemplated.

The materials used in the system 20 are surgical grade metals or polymers. For example, the implantable suture anchor 46 and bone anchoring element 48 may be made of a biocompatible polymer such as polyethylene or a metal such as titanium. The suture locking elements 62a, 62b are desirably metal, although certain hard plastics or polycarbonates may be used. The materials of the devices used to implant the anchor 46, such as insertion tubes 52, 56, need not be as durable as the implantable materials. The anchors may also be fabricated from bio-absorbable materials commonly used for implantation such as polyglycolide (PGA), polylactide (PLA), homopolymer of 1-lactide (LPLA), or other bio-absorbable materials known in the art.

In use of the system 20, the various components as described above are first procured and assembled. The surgeon creates the operating ports necessary in the dermal layers and forms the body cavity 40 in the humeral head 24 as seen in FIGS. 1A and 1B. The hole 40 has been drilled in the bone at the location chosen by the surgeon for anchor fixation. The delivery system 50 is inserted through one of the operating ports, and the shoulder 54 of the introducer tube 56 is positioned within the hole 40. By pushing on the deployment tube 52, the anchor 46 is forced out of the introducer tube 46 and down into the hole 40. The shoulder 54 of the introducer tube 46 ensures that the anchor 46 is delivered into the hole 40 below the hard outer layer of cortical bone 42 so that the anchoring member 48 can bear upon the cortical bone 42.

FIGS. 8 and 9 further illustrate the suture-locking function of the present invention along longitudinal sections, and also show the entire bone anchoring and suture-tightening aspects. In FIG. 8, the suture loop 32 can be considered to be embedded in soft tissue, and thus relatively securely positioned. The bone anchoring member 48 has been deployed such that its flat proximal surface abuts the inside wall of a body cavity, such as the inside wall of the hard cortical bone 42 of the humeral head 24, as previously described.

The suture anchor system 20 including the delivery tube 52 remains in place held against the bone anchoring member 48 by the locking plugs 68a, 68b and the tension in the actuation rods 70. Because the locking plugs 68a, 68b remain in their distal position, the suture-locking elements 62a, 62b are un-deployed in their first positions and the lengths of suture 34a, 34b are free to slide within the passage 94.

At this stage, the surgeon adjusts the tension in the lengths of suture 34a, 34b by pulling on the free ends 34a', 34b', or pulling on one end while holding one fixed, in the direction of arrow 120 in FIG. 8. Adjustment of the length of the suture between the suture anchor 46 and the loop 32 is very important to ensure proper fixation of the rotator cuff tendon 22 with respect to the humeral head 24. If the suture is pulled too tightly, the rotator cuff tendon 22 may be unduly stressed, and the loop 32 may even pull free from the tendon. On the other hand, if the suture is too loose, the goal of reattaching the tendon 22 in its proper location will be compromised.

As mentioned above, the lengths of suture 34a, 34b wrap around the cross member 92 (see FIG. 5A) which acts as a pulley of sorts and permits the sutures to freely slide therepast. The result of pulling on the free ends 34a', 34b' is to pull the portions between the system 20 and the loop 32 taught. This is also depicted in FIG. 1D. The particular tension established in the sutures 34a, 34b depends on the patient characteristics, the type of soft tissue being reattached, and surgeon judgement.

After adjusting the tension of the sutures 34a, 34b, the actuation rods 70 are displaced in a proximal direction, as indicated at 122 in FIG. 9. As described above, this step causes the suture-locking elements 62a, 62b to cam inward and reduce the size of the passage, clamping the sutures 34a, 34b in between an irregular pattern of "teeth." The cross sectional view of FIG. 9A shows the resulting clamped configuration of the sutures 34a, 34b.

One advantage provided by the present invention is the ability to tighten a suture loop embedded within soft tissue to a predetermined tension, and then lock the suture within a suture anchor without even slightly altering that tension. Importantly, because the suture-locking elements 62a, 62b are displaced radially, they do not urge the sutures 34a, 34b to migrate axially within the tubular anchor body 60, and therefore do not change the length on either side of the cross member 92. This ensures that the proper tension established between the suture anchor 46 and the loop 32 embedded in the soft tissue does not change.

Subsequently, the actuation rods 70 are detached from the suture-locking plugs 68a, 68b by further pulling in the direction of arrows 122, thus causing a point of weakness to sever. The point of weakness is not shown, but typically comprises a narrow neck or frangible point on each rod 70 disposed just proximal to, or within a bore of, the corresponding locking plug 68a or 68b. At this stage, the concentric tubes 52, 54, 56 can be removed from the operation site and the sutures 34a, 34b severed close to the bore 82 of the bone anchoring member 48. After any further post-procedure steps, the site of the operation can then be closed.

The distal end of an alternative bone anchoring and suture locking system 130 is shown in FIGS. 11–12B and includes a tubular anchor body 132 housing a plurality of identical suture-locking elements 134. FIG. 11 also shows the two free ends of a length of suture 136 extending through the anchor body 132 on one side and wrapping around at a distal loops 138 to continue through the body on the opposite side. The cross-sectional view in FIG. 12A illustrates the location of the four strands of the suture 136. Although not shown, the distal loops 138 wrap around a cross member or pulley fixed with respect to the anchor body 132, as in the earlier-described embodiment.

A suture-locking plug 140 attached to an actuation rod 142 is initially located at the distal end of the stack of suture-locking elements 134. The actuation rod 142 passes through a partially aligned series of central apertures 144 in the suture-locking elements 134, as seen in FIG. 12A. In this regard, there are a plurality of configurations of suture-locking elements 134 that differ only in the location of the central aperture 144. Desirably, there is a single shape of element 134 having a central aperture 144 that is offset from but overlapping the central axis. Adjacent elements 134 are oriented in opposite directions so that their apertures 144 are offset in opposite directions. The aligned portions of the apertures 144 are large enough for passage of the actuation rod 142, though smaller than the locking plug 140.

In use, the suture-locking elements 134 are initially in first positions as seen in FIG. 12A. The outer edge of each element 134 has two diametrically-opposed cavities 146 that are sized to receive two of the suture strands 136. The cavities 146 form axially-uniform tunnels with the inner wall of the tubular anchor body 132 that permit the free ends of the sutures to pass easily therethrough, and thus facilitate the suture tensioning step as explained above. Unlike the earlier embodiment, the tunnels have the an entirely uniform cross-section along their axial length, as seen in FIG. 12A.

Proximal displacement of the actuation rod 142 and attached locking plug 140 forces a taper at the leading or proximal end of the locking plug into the partially aligned apertures 144, thus camming alternating elements 134 in opposite radial directions into second positions. That is, the locking plug 140 lies on the central axis of the system, and thus each offset aperture 144 is forced toward the axis as well. The size of each aperture 144 is just large enough to permit passage of the locking plug 140, and thus the final configuration as seen in FIG. 12B has the apertures 144 aligned concentrically about the locking plug along the central axis.

FIG. 12B also shows the clamping of the lengths of suture by the outward movement of each suture-locking element 134. Because only every other one of the elements 134 clamps each pair of suture strands, there is again an irregular passage created. That is, each pair of two strands of suture is compressed against the inner wall of the tubular anchor body 132 by a series of spaced apart edges of the cavities 146 of every second element 134. The tunnels formed by the cavities 146 and the inner wall of the tubular anchor body 132 are thus reduced in size and rendered non-uniform.

FIGS. 11–11B also show an alternative bone anchoring structure. Rather than a single bone anchoring member, such as member 48 seen in FIG. 2, the system 130 has a plurality of relatively thin bone anchoring members 150 that are stacked axially together. This bone anchoring system is described in co-pending application Ser. No. 09/876,260 filed Jun. 6, 2001, which has already been expressly incorporated by reference herein. Each member 150 has a V-shape prior to deployment, as seen in FIG. 11, and has a generally oval outer profile as seen in plan view in FIG. 11B. Two off-center apertures 152 in each member 150 permit passage of the strands of suture. A central aperture 154 permits passage of the actuation rod 142.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention. In particular, it is noted that the procedures, while oriented toward the arthroscopic repair of the rotator cuff, are applicable to the repair of any body location wherein it is desired to attach or reattach soft tissue to bone, particularly using an arthroscopic procedure.

What is claimed is:

1. A knotless suture anchor apparatus for anchoring a length of suture with respect thereto, comprising:

an anchor body having a proximal end, a distal end, and a lumen opening at the proximal end such that a length of suture may be introduced into the lumen from the proximal end;

bone anchoring structure for securing said anchor body within adjacent bone; and a plurality of suture-locking elements located within the anchor body lumen and each movable within the lumen from respective first positions to second positions, the locking elements in their first positions together defining a generally uniform cross-section axial passage sized to permit axial movement of the length of suture therethrough, and in their second positions converting the cross-section of the axial passage to be irregular and therefore substantially restrict axial movement of the length of suture therethrough.

2. The apparatus of claim 1, wherein the axial passage is located generally in the center of the lumen and the suture-locking elements each move toward the center of the lumen from their first to their second positions.

3. The apparatus of claim 2, wherein the suture-locking elements are substantially C-shaped and each surrounds and defines approximately three-quarters of the axial passage.

4. The apparatus of claim 2, wherein at least one of the suture-locking elements moves in a different direction than the others from their respective first to their second positions.

5. The apparatus of claim 1, wherein the suture-locking elements are arranged to move radially within the lumen from their first to their second positions.

6. The apparatus of claim 5, and further including:

a suture-locking plug that is axially displaceable within the lumen so as to contact at least some of the suture-locking elements and move them from their first to their second positions.

7. A knotless suture anchor apparatus for anchoring a length of suture with respect to a body cavity, comprising:

an anchor body having a proximal end, a distal end, and a lumen opening at the proximal end such that a length of suture may be introduced into the lumen from the proximal end, the anchor body being sized to fit within the body cavity;

bone anchoring structure for securing said anchor body within adjacent bone; and a plurality of suture-locking elements radially movable within the lumen from respective first positions to second positions, the locking elements in their first positions together defining at least one axial passage sized to permit axial movement of the length of suture therethrough, and in their second positions reducing the size of the passage so as to clamp the length of suture therein and substantially restrict axial movement of the length of suture therethrough.

8. The apparatus of claim 7, wherein the axial passage is located generally in the center of the lumen and the suture-locking elements each move toward the center of the lumen from their first to their second positions.

9. The apparatus of claim 8, wherein the suture-locking elements are substantially C-shaped and each surrounds and defines approximately three-quarters of the axial passage.

10. The apparatus of claim 8, wherein at least one of the suture-locking elements moves in a different direction than the others from their respective first to their second positions.

11. The apparatus of claim 7, and further including:
a suture-locking plug that is axially displaceable within the lumen so as to contact at least one of the suture-locking elements and move it from its first to its second position.

12. The apparatus of claim 7, wherein the anchor body further includes a suture return member fixed with respect thereto such that the length of suture may be passed into lumen from the proximal end, through the axial passage, looped around the suture return member, back through the axial passage, and passed out of the lumen through the proximal end.

13. A method of securing soft tissue with respect to a body cavity without knots, comprising:
passing a length of suture through soft tissue so that a loop of suture material is embedded in the soft tissue resulting in two free ends;
providing an anchor body having an open proximal end and a lumen, and a plurality of suture-locking elements located within the anchor body lumen and each movable within the lumen from respective first positions to second positions, the locking elements in their first positions together defining a generally uniform cross-section axial passage sized to permit axial movement of the length of suture therethrough, and in their second positions converting the cross-section of the axial passage to be irregular and therefore substantially restricting axial movement of the length of suture therethrough;
passing the two free ends of the length of suture into the lumen of the anchor body through the open proximal end and through the passage with the suture-locking elements in their first positions, and extending the two free ends out of the lumen through the open proximal end;
fixing the anchor body with respect to a body cavity;
tightening the loop of suture material by pulling on one or both of the two free ends of the length of suture; and
fastening the two free ends of the length of suture with respect to the anchor body without the use of knots by displacing the suture-locking elements to their second positions.

14. The method of claim 13, wherein the soft tissue is a tendon, and the body cavity is formed in a bone.

15. The method of claim 14, wherein the tendon is the rotator cuff tendon, and wherein the bone is the humeral head.

16. The method of claim 13, wherein the step of fixing the anchor body with respect to the body cavity comprises forming the body cavity, passing the anchor body into the body cavity, and radially expanding anchoring structure on the anchor body.

17. The method of claim 16, wherein the body cavity is a cylindrical tunnel formed in a bone, and wherein the anchoring structure is provided on a proximal end of the anchor body so as to interfere with the cortical layer of the bone and prevent proximal removal of the anchor body from the cylindrical tunnel.

18. The method of claim 13, and further including a step of providing a suture-locking plug that is axially displaceable within the lumen so as to contact at least some of the suture-locking elements and move them from their first to their second positions.

19. The method of claim 18, wherein at least one of the suture-locking elements moves in a different direction than the other suture-locking elements, from their respective first to their second positions, said suture-locking plug being displaced axially to move the suture-locking elements in different directions.

20. The method of claim 18, wherein at least one of the suture-locking elements moves in the opposite direction of the other suture-locking elements, from their first to their second positions, said suture-locking plug providing step including providing two suture-locking plugs, said two suture-locking plugs being axially displaced to move different suture-locking elements in opposite directions.

21. A knotless suture anchor apparatus for anchoring a length of suture with respect thereto, comprising:
an anchor body having a proximal end, a distal end, and a lumen opening at the proximal end such that a length of suture may be introduced into the lumen from the proximal end; and
a plurality of substantially C-shaped suture-locking elements located within the anchor body lumen and each movable within the lumen from respective first positions to second positions, the locking elements in their first positions together defining a generally uniform cross-section axial passage sized to permit axial movement of the length of suture therethrough, and in their second positions converting the cross-section of the axial passage to be irregular and therefore substantially restrict axial movement of the length of suture therethrough;
wherein the axial passage is located generally in the center of the lumen and the suture-locking elements each surround and define approximately three-quarters of the axial passage and move toward the center of the lumen from their first to their second positions.

22. A knotless suture anchor apparatus for anchoring a length of suture with respect thereto, comprising:
an anchor body having a proximal end, a distal end, and a lumen opening at the proximal end such that a length of suture may be introduced into the lumen from the proximal end; and
a plurality of suture-locking elements located within the anchor body lumen and each movable within the lumen from respective first positions to second positions, the locking elements in their first positions together defining a generally uniform cross-section axial passage sized to permit axial movement of the length of suture therethrough, and in their second positions converting the cross-section of the axial passage to be irregular and therefore substantially restrict axial movement of the length of suture therethrough;
wherein the axial passage is located generally in the center of the lumen and the suture-locking elements each move toward the center of the lumen from their first to their second positions and further wherein at least one of the suture-locking elements moves in a different direction than the others from their respective first to their second positions.

23. The apparatus of claim 22, wherein there are at least three suture-locking elements that are stacked axially and arranged to move radially within the lumen, and wherein adjacent suture-locking elements move in opposite directions.

24. The apparatus of claim 23, wherein the suture-locking elements are substantially C-shaped and each surrounds and defines approximately three-quarters of the axial passage.

25. The apparatus of claim 22, and further including:
a pair of suture-locking plugs that are axially displaceable within the lumen so as to contact different suture-locking elements and move them in different directions from their first to their second positions.

26. A knotless suture anchor apparatus for anchoring a length of suture with respect thereto, comprising:
an anchor body having a proximal end, a distal end, and a lumen opening at the proximal end such that a length of suture may be introduced into the lumen from the proximal end;
a plurality of suture-locking elements located within the anchor body lumen and each movable within the lumen from respective first positions to second positions, the locking elements in their first positions together defining a generally uniform cross-section axial passage sized to permit axial movement of the length of suture therethrough, and in their second positions converting the cross-section of the axial passage to be irregular and therefore substantially restrict axial movement out of the length of suture therethrough; and
a suture-locking plug that is axially displaceable within the lumen so as to contact at least some of the suture-locking elements and move them from their first to their second positions.

27. The apparatus of claim 26, wherein there are at least three suture-locking elements that are stacked axially and arranged to move radially within the lumen, and wherein adjacent suture-locking elements move in opposite directions.

28. A knotless suture anchor apparatus for anchoring a length of suture with respect to a body cavity, comprising:
an anchor body having a proximal end, a distal end, and a lumen opening at the proximal end such that a length of suture may be introduced into the lumen from the proximal end, the anchor body being sized to fit within the body cavity; and
a plurality of suture-locking elements radially movable within the lumen from respective first positions to second positions, the locking elements in their first positions together defining at least one axial passage sized to permit axial movement of the length of suture therethrough, and in their second positions reducing the size of the passage so as to clamp the length of suture therein, the axial passage being located generally in the center of the lumen and the suture-locking elements each moving toward the center of the lumen from their first to their second positions;
wherein the suture-locking elements are substantially C-shaped and each surrounds and defines approximately three-quarters of the axial passage.

29. A knotless suture anchor apparatus for anchoring a length of suture with respect to a body cavity, comprising:
an anchor body having a proximal end, a distal end, and a lumen opening at the proximal end such that a length of suture may be introduced into the lumen from the proximal end, the anchor body being sized to fit within the body cavity; and
a plurality of suture-locking elements radially movable within the lumen from respective first positions to second positions, the locking elements in their first positions together defining at least one axial passage sized to permit axial movement of the length of suture therethrough, and in their second positions reducing the size of the passage so as to clamp the length of suture therein, the axial passage being located generally in the center of the lumen and the suture-locking elements each moving toward the center of the lumen from their first to their second positions;
wherein at least one of the suture-locking elements moves in a different direction than the others from their respective first to their second positions.

30. The apparatus of claim 29, and further including:
a pair of suture-locking plugs that are axially displaceable within the lumen so as to contact different suture-locking elements and move them in opposite directions from their first to their second positions.

31. A knotless suture anchor apparatus for anchoring a length of suture with respect to a body cavity, comprising:
an anchor body having a proximal end, a distal end, and a lumen opening at the proximal end such that a length of suture may be introduced into the lumen from the proximal end, the anchor body being sized to fit within the body cavity;
a plurality of suture-locking elements radially movable within the lumen from respective first positions to second positions, the locking elements in their first positions together defining at least one axial passage sized to permit axial movement of the length of suture therethrough, and in their second positions reducing the size of the passage so as to clamp the length of suture therein; and
a suture-locking plug that is axially displaceable within the lumen so as to contact at least one of the suture-locking elements and move it from its first to its second position.

32. The apparatus of claim 31, wherein the suture-locking plug has a first cross-sectional size and further including an actuation rod having a second cross-sectional size smaller than the first, the actuation rod being removably attached to the proximal end of the suture-locking plug and projecting out of the proximal end of the anchor body, the actuation rod being used to displace the suture-locking plug axially within the lumen.

33. The apparatus of claim 32, and further including a point of tensile weakness along the actuation rod, thereby permitting the wire to be detached from the suture-locking plug upon application of a predetermined tensile force on the actuation rod in the proximal direction after each of the at least one contacted suture-locking elements have moved from their respective first positions to their respective second positions.

34. The apparatus of claim 31, wherein there are at least two suture-locking elements that are stacked axially and arranged to move radially within the lumen, and wherein adjacent suture-locking elements move in opposite directions.

35. The apparatus of claim 31, wherein there are two of the axial passages and two lengths of suture, each located on diametrically opposed sides of the lumen and against the anchor body wall, wherein the suture-locking elements each move toward one of the axial passages when displaced from their first to their second positions.

36. The apparatus of claim 35, wherein each suture-locking element has an aperture offset from the center of the lumen, which the suture-locking plug contacts to displace the suture-locking element, the apertures of adjacent suture-locking elements being offset in different directions such that axial displacement of the suture-locking plug moves adjacent elements in different directions.

37. A knotless suture anchor apparatus for anchoring a length of suture with respect to a body cavity, comprising:

an anchor body having a proximal end, a distal end, and a lumen opening at the proximal end such that a length of suture may be introduced into the lumen from the proximal end, the anchor body being sized to fit within the body cavity;

a plurality of suture-locking elements radially movable within the lumen from respective first positions to second positions, the locking elements in their first positions together defining at least one axial passage sized to permit axial movement of the length of suture therethrough, and in their second positions reducing the size of the passage so as to clamp the length of suture therein;

wherein the anchor body further includes a suture return member fixed with respect thereto such that the length of suture may be passed into the lumen from the proximal end, through the axial passage, looped around the suture return member, back through the axial passage, and pased out of the lumen through the proximal end.

* * * * *